(12) United States Patent
Kocaturk

(10) Patent No.: US 9,486,158 B2
(45) Date of Patent: Nov. 8, 2016

(54) ACTIVE ADAPTIVE DETUNING SYSTEMS AND METHODS FOR INTERVENTIONAL DEVICES

(75) Inventor: Ozgur Kocaturk, Rockville, MD (US)

(73) Assignee: The United States of America, as Represented by the Secretary, Department of Health and Human Services, Washington, DC (US)

( * ) Notice: Subject to any disclaimer, the term of this patent is extended or adjusted under 35 U.S.C. 154(b) by 645 days.

(21) Appl. No.: 13/805,454

(22) PCT Filed: Jul. 1, 2011

(86) PCT No.: PCT/US2011/042746
§ 371 (c)(1),
(2), (4) Date: Mar. 21, 2013

(87) PCT Pub. No.: WO2012/003422
PCT Pub. Date: Jan. 5, 2012

(65) Prior Publication Data
US 2013/0172729 A1 Jul. 4, 2013

Related U.S. Application Data

(60) Provisional application No. 61/360,998, filed on Jul. 2, 2010.

(51) Int. Cl.
*A61B 5/055* (2006.01)
*G01R 33/36* (2006.01)
(Continued)

(52) U.S. Cl.
CPC ........... *A61B 5/055* (2013.01); *G01R 33/3657* (2013.01); *G01R 33/285* (2013.01); *G01R 33/34084* (2013.01)

(58) Field of Classification Search
CPC ................ A61B 5/055; G01R 33/285; G01R 33/34084; G01R 33/3657
See application file for complete search history.

(56) References Cited

U.S. PATENT DOCUMENTS

2004/0220470 A1* 11/2004 Karmarkar et al. .......... 600/423
2006/0106303 A1* 5/2006 Karmarkar et al. .......... 600/422
(Continued)

FOREIGN PATENT DOCUMENTS

| EP | 0164164 A1 | 12/1985 |
|---|---|---|
| EP | 0315382 A2 | 5/1989 |
| WO | 2008/020375 A1 | 2/2008 |

OTHER PUBLICATIONS

Liu, Y., et al., "Numerical investigations of MRI RF field induced heating for external fixation devices," BioMedical Engineering OnLine, 2013, 12:12, pp. 1-14.
(Continued)

*Primary Examiner* — Ruth S Smith
(74) *Attorney, Agent, or Firm* — Polsinelli PC; Ron Galant

(57) ABSTRACT

Active MRI compatible interventional devices, such as catheters, include at least one RF antenna so that they are visible under MRI analysis. However, metallic structures within intravascular devices may heat up significantly during interventional MRI procedures due to eddy current formation over the conductive transmission lines. The electrical field coupling that occurs between interventional devices and RF signals depend on the position and orientation of interventional device within the bore and the insertion length of the interventional device. The system detects an induced current signal during RF transmission phase and selectively adjusts the impedance value associated with the interventional device by using a varactor and integrated circuit components in such a manner that the currents induced in the interventional device are below a threshold current level, thereby controlling current levels and heating in the interventional device.

9 Claims, 5 Drawing Sheets

(51) Int. Cl.
  *G01R 33/28* (2006.01)
  *G01R 33/34* (2006.01)

(56) References Cited

U.S. PATENT DOCUMENTS

2007/0118335 A1* 5/2007 Andarawis et al. .......... 702/188
2008/0272786 A1* 11/2008 Luedeke et al. .............. 324/322

OTHER PUBLICATIONS

Sonmez, M., et al., "MRI active guidewire with an embedded temperature probe and providing a distinct tip signal to enhance clinical safety," Journal of Cardiovascular Magnetic Resonance, 2012, 14:38, pp. 1-10.

Kocaturk, O., et al., "An active two channel 0.035 guidewire for interventional cardiovascular MRI," J. Magn. Reson. Imaging, Aug. 2009, 30(2), pp. 461-465.

Zaremba, L.A., FDA Guidelines for Magnetic Resonance Equipment Safety, Handout presented at the 44th American Association of Physicists in Medicine Annual Meeting (Jul. 16, 2002).

ASTM International, Standard Test Method for Measurement of Radio Frequency Induced Heating on or Near Passive Implants During Magnetic Resonance Imaging, F2182-09 (Jan. 2010).

Non-Clinical Engineering Tests and Recommended Labeling for Intravascular Stents and Associated Delivery Systems, U.S. Dept. Health and Human Services, Food and Drug Administration, Center for Devices and Radiological Health (Apr. 18, 2010).

Gorny, K.R. et al., Measurements of RF Heating During 3.0T MRI of a Pig Implanted With a Deep Brain Stimulator, Magn. Reson. Imaging, 31(5):1-17 (Jun. 2013).

Mattei E. et al., Complexity of MRI Induced Heating on Metallic Leads: Experimental Measurements of 374 Configurations, BioMedical Engineering OnLine, 7:11, 1-16 (Mar. 3, 2008).

Nordbeck, P. et al., Measuring RF-Induced Currents Inside Implants: Impact of Device Configuration on MRI Safety of Cardiac Pacemaker Leads, Magnetic Resonance in Medicine, 61:570-578 (Jan. 8, 2009).

* cited by examiner

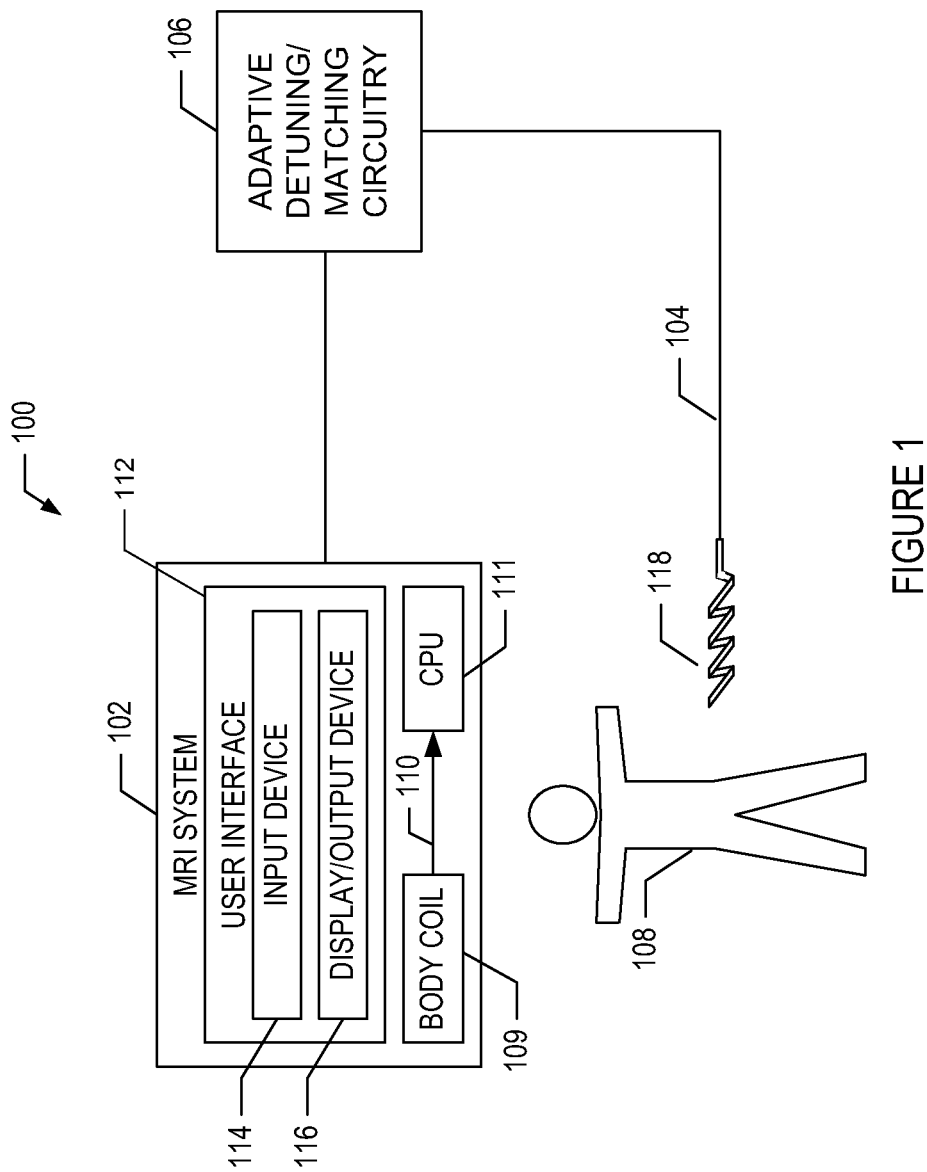

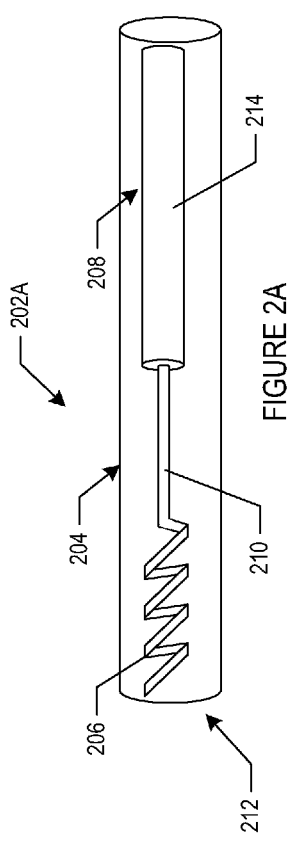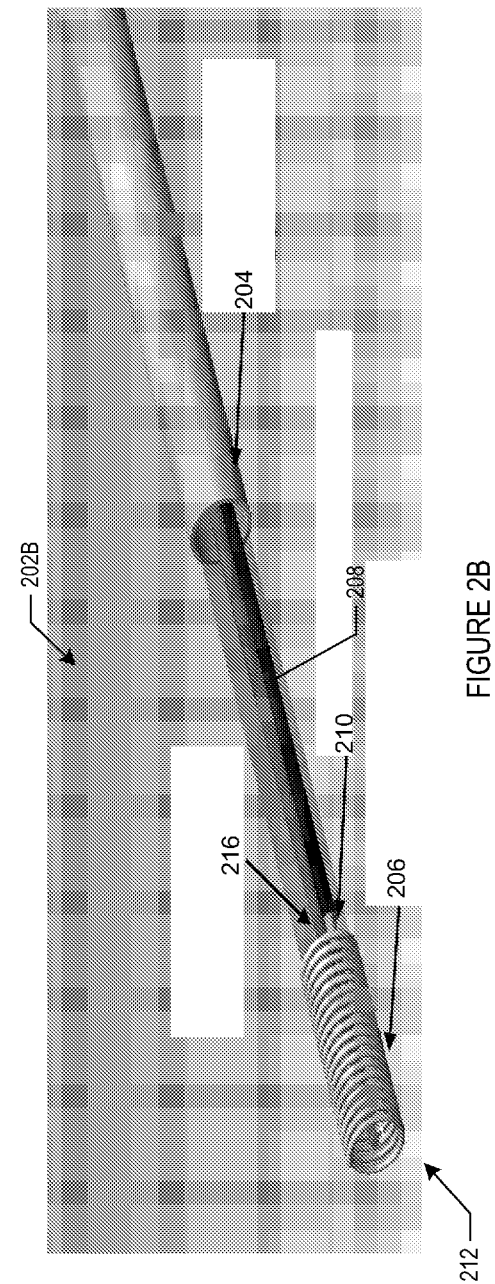
FIGURE 2A
FIGURE 2B

ACTIVE ADAPTIVE DETUNING SYSTEMS AND METHODS FOR INTERVENTIONAL DEVICES

RELATED APPLICATIONS

This application takes priority to U.S. Patent Application No. 61/360,998, filed Jul. 2, 2010, and entitled Active Adaptive Detuning Systems and Methods for Interventional Devices, the entire contents of which are incorporated herein by reference.

FEDERALLY SPONSORED RESEARCH OR DEVELOPMENT

Not Applicable.

COMPACT DISK APPENDIX

Not Applicable.

BACKGROUND

Magnetic resonance imaging (MRI) is a well-established medical imaging and diagnostic tool. A great deal of current activity and research relates to interventional and/or intraoperative procedures conducted under MRI guidance (iMRI). In many interventional and intraoperative procedures under MRI guidance, surgical devices such as long needles, guidewires, and catheters are inserted into a subject undergoing MRI analysis. Such procedures enable surgeons to image, locate, and track such devices during a MRI procedure. To enable such tracking in real time during a MRI procedure, interventional devices are typically equipped with a radio frequency (RF) antenna, more particularly an RF coil.

The RF coil is typically located at the distal end of the catheter or other device and receives a RF signal emitted from excited protons of blood or tissue in its vicinity when they return to equilibrium. The RF coils sends an electrical signal directly to the MRI scanner by way of an attached coaxial cable. The coaxial cable is typically a very thin coaxial cable that runs through a lumen in the catheter. The presence of long conductive objects, such as coaxial cables, has been found to lead to heating at the tip of the device. Medical studies indicate that this effect is due to coupling of the RF field from the MRI system, primarily to long cables or transmission lines, i.e., longer than one quarter of the RF wavelength within the body (approximately 80 cm), couples significantly with the RF transmission energy of the body coil of the MRI system. Examples articles that discuss such studies include "Reduction of Resonant RF Heating in Intravascular Catheters Using Coaxial Chokes", Mark E. Ladd et al., Magnetic Resonance in Medicine 43:61-5-619 (2000); "RF Safety of Wires in Interventional MRI: Using a Safety Index", Christopher J. YEUNG et al., Magnetic Resonance in Medicine 47:187-193 (2002); "RF Heating Due to Conductive Wires During MRI Depends on the Phase Distribution of the Transmit Field", Christopher J. YEUNG et al., Magnetic Resonance in Medicine 48:1096-1098 (2002); and "Safety of MRI-Guided Endovascular Guidewire Applications", Chia-Ying LIU et al. Journal of Magnetic Resonance Imaging 12:75-78 (2000)). These studies indicate that long transmission cables, even without the RF coil, show significant heating, whereas, RF coils without the cable show no heating.

Although decoupling circuits have been used at the proximal end of the catheter to reduce the electric field coupling, such circuits do not work well when the conductor length increases (e.g., exceeds 80 cm). Because of this heating problem, active MRI compatible and visible catheters are currently used only in animal studies. Consequently, there is a need for improved active MRI compatible devices that do not have a severe heating problem.

SUMMARY

According to one aspect, a system is provided for use during a magnetic resonance imaging procedure. The system includes a magnetic resonance imaging device to selectively apply a radio frequency radiation signal across a selected portion of a subject and discontinue application of the radio frequency radiation signal across the selected portion of the subject. The system also includes an interventional device for insertion into the subject proximate to the selected portion of the subject. The interventional device includes a radio frequency antenna at a distal end of the interventional device to receive an induced current based on another radio frequency signal emitted from tissue surrounding the radio frequency antenna when the interventional device is inserted in the subject. The interventional device also includes an inner conductor along a length of the interventional device that is connected to the radio frequency antenna to conduct the induced current. The system also includes an adaptive detuning circuit that is connected to the inner conductor to iteratively adjust an impedance value of the interventional device through each of a plurality of impedance values. The adaptive detuning circuit also determines a corresponding magnitude of the induced current in the inner conductor for each of the plurality of impedance values. The adaptive detuning circuit also sets the impedance value of the interventional device to a first one of the plurality of impedance values where the corresponding magnitude of the induced current is below a threshold current level. The threshold current level may be retrieved from a memory.

According to another aspect, an adaptive detuning circuit is provided for use in a magnetic resonance system during insertion of an interventional device into a subject during a magnetic resonance imaging procedure. The magnetic resonance imaging system selectively applies and discontinues application of a radio frequency radiation signal across a selected portion of a subject. The interventional device includes a radio frequency antenna to receive an induced current based on another radio frequency signal emitted from tissue proximate to the radio frequency antenna. The interventional device also includes an inner conductor connected to the radio frequency antenna to conduct the induced current conductor. The adaptive detuning circuit includes a connector to connect to the inner conductor. The adaptive detuning circuit also includes a control circuit to iteratively adjust an impedance value of the interventional device through each of a plurality of impedance values. The control circuit also determines a corresponding magnitude of the induced current in the inner conductor for each of the plurality of impedance values. The control circuit further sets the impedance value of the interventional device to a first one of the plurality of impedance values where the corresponding magnitude of the induced current is below a threshold current level. The threshold current level may be retrieved from a memory.

According to another aspect, a method is provided for adjusting an impedance value associated with an interventional device during insertion of the interventional device into a subject during a magnetic resonance imaging procedure. The method includes inserting an interventional device having an inner conductor and a radio frequency antenna into the subject. The method also includes applying a radio frequency radiation signal across a selected portion of a subject via a magnetic resonance imaging device. The method also includes discontinuing application of the radio frequency radiation signal across the selected portion of the subject. The method also includes receiving an induced current in the conductor via the radio frequency antenna based on another radio frequency signal emitted from tissue surrounding the radio frequency antenna when application of the radio frequency radiation signal is discontinued. The method also includes iteratively adjusting an impedance value of the interventional device through a plurality of impedance values. The method also includes determining a corresponding magnitude of the induced current in the inner conductor for each of the plurality of impedance values. The method also includes setting the impedance value of the interventional device to a first one of the plurality of impedance values where the corresponding magnitude of the induced current is below a threshold current level. The method may also include retrieving the threshold current level from a memory.

BRIEF DESCRIPTION OF THE DRAWINGS

FIG. 1 is a block diagram that depicts an exemplary embodiment of the active adaptive detuning system (AADS).

FIGS. 2A and 2B depict exemplary interventional devices according to an aspect of the AADS.

DETAILED DESCRIPTION

Figure 3:
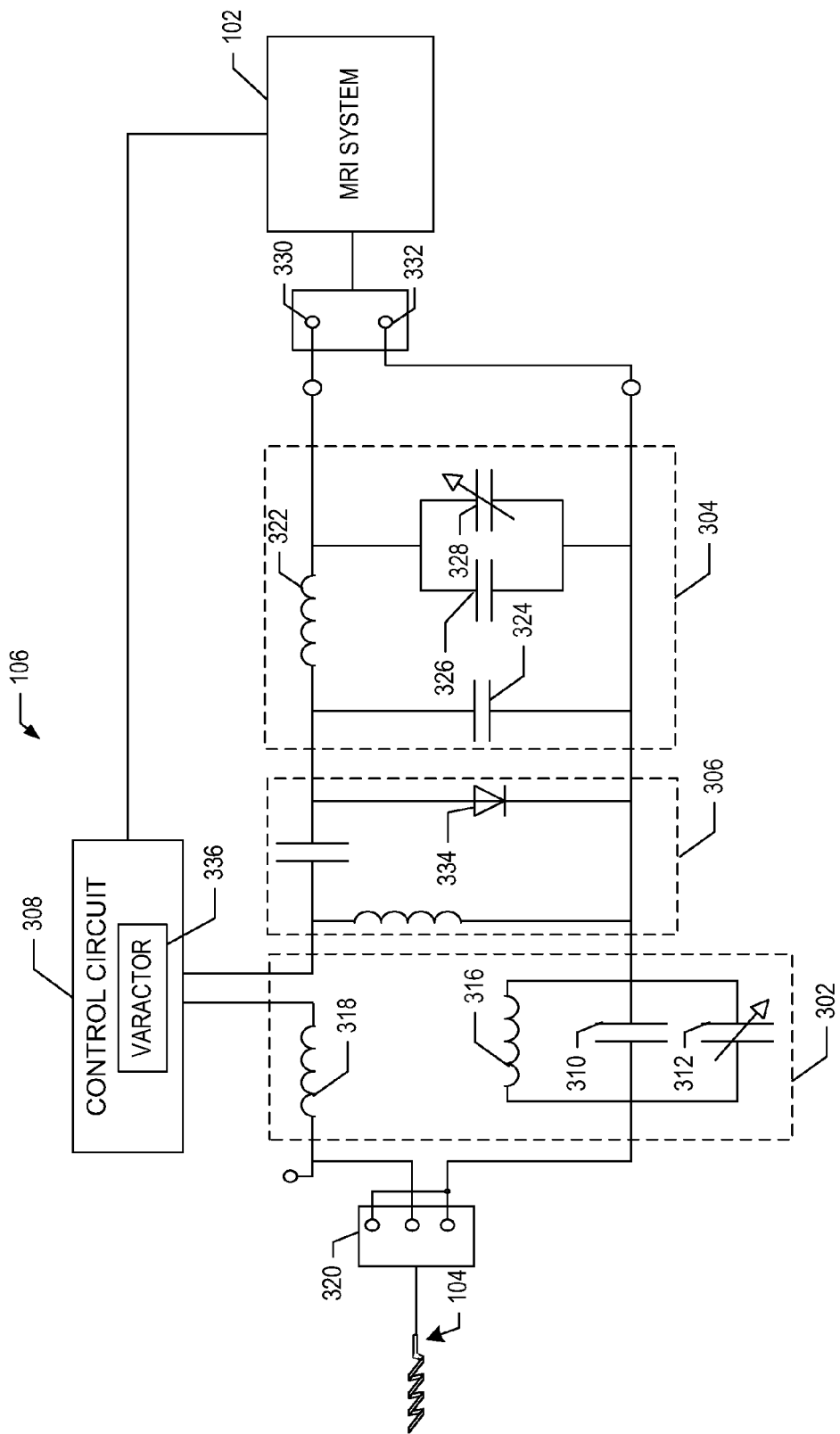
FIG. 3 depicts circuit components of an adaptive detuning circuit according to one aspect of the active adaptive detuning system.

Medical devices, such as catheters, catheter guide wires, endoscopes, and/or other interventional surgical devices (interventional devices), are often inserted into the body of a subject undergoing imaging analysis with MRI system, such as a MRI scanner. Active MRI compatible interventional devices often include at least one RF antenna so that they are visible under MRI analysis. Such wire-like conductive structures interact with the radio-frequency fields in the MRI system, and under certain conditions an RF signal, such as electrical currents and/or voltages can be induced in these structures. The RF current induced on the interventional device can cause local heating of tissue adjacent to the interventional device during the MRI procedure, which can potentially lead to undesired tissue damage within the subject. Aspects of the active adaptive detuning system described herein control and limit these currents and/or voltages by interfering with the resonant conditions that can lead to larger currents and/or voltages and electric fields.

Aspects of the active adaptive detuning system described herein also enable dynamic adjustment of an amount of current and/or voltage induced within an interventional device when exposed to an external radio-frequency field produced, for example, by a MRI scanner. The amount of current and/or voltage induced on an interventional device can vary based on an orientation and/or an insertion length of the interventional device within the body. The AAD System and Method dynamically adjusts an amount of current and/or voltage induced within an interventional device when it is exposed to an external RF produced, for example, by a MRI scanner. In particular, the AAD System and Method enables automatic adjustment of the impedance of the interventional device to maintain the RF signal generated in the interventional device within a target current and/or voltage range and, thus, limit an amount of heat generated by the interventional device when inside the body.

FIG. 1 depicts an exemplary embodiment of the active adaptive detuning system (AADS) 100. The AADS 100 includes an MRI system 102, an interventional device 104, and an adaptive tuning/matching circuit 106.

The MRI system 102 is, for example, a MRI scanner that enables the visualization of organs, organ function, and/or other tissue within a body of a subject 108, such as a patient. The MRI system 102 includes a primary magnet (not shown) that generates a uniform magnetic field that is applied across the body of the subject under observation. The MRI system 102 also includes smaller gradient magnets (not shown) that allow the magnetic field to be altered very precisely. The gradient magnets allow image "slices" of the body to be created. By altering the gradient magnets, the magnetic field can be specifically focused on a selected part of the body.

After the subject is properly positioned for analysis by the MRI system 102 and the primary magnet is activated, the nuclei of the hydrogen atoms with the body of the subject 108 begin spinning. The MRI system 102 includes a body coil 109 that emits a radio frequency (RF) radiation signal. The emitted RF signal causes the nuclei within the body of the subject 108 to transition their spin orientation, or precess. The frequency of the energy at which this transition occurs is known as the Larmor Frequency. When the body coil 109 is not providing the RF signal, the hydrogen nuclei hydrogen atoms transition back to a lower energy state and reemits the electromagnetic energy at the RF wavelength. The body coil 109 of the MRI system 102 detects the RF energy emitted by the hydrogen nuclei and generates an image signal 110.

The MRI system 102 includes a central processing unit 111, such as a computer, processor, or other processing device, to receive and process the image signal 110 and create images to display via a user interface 112. The user interface 112 includes, for example, one or more input devices 114, along with one or more displays or output devices 116. In a typical application, the input device 114 will include a conventional operator keyboard, or other operator input devices for selecting image types, image slice orientations, configuration parameters, and so forth. The display/output device 116 will typically include a computer monitor for displaying the operator selections, as well as for viewing scanned and reconstructed images. Such devices may also include printers or other peripherals for reproducing hard copies of the reconstructed images. The central processing unit 111 communicates also with the user interface 112 to receive input data from a user and/or to provide image data to the user.

According to one aspect, the central processing device 111 processes the image signal 110 to perform 2D Fourier transforms to convert the acquired data from the time domain to the frequency domain, and to reconstruct the data into a meaningful image. The image signal 110 may indicate different resonance characteristics for different tissue types. For example, the different resonance characteristics produced from a particular organ are displayed in an image in different of shades of grey, such that some body tissues show up darker or lighter as compared to other body tissues. As another example, the different resonance characteristics produced from a particular organ can be displayed in an image as different colors or displayed as different contrast of a particular color.

During MRI analysis of a subject 108, the interventional device 104 can be introduced into the subject 108 via, for example, a vascular structure within the body of the subject 108. According to one aspect, and as described in more detail below in reference to FIG. 2, the interventional device 104 includes flexible tubing or a lumen that extends along the length of the interventional device 104. The interventional device 104 may also include a RF coil 118 that is positioned or formed at the distal end of the interventional device 104. The RF coil 118 operates as an antenna and is matched and tuned to the Larmor frequency of the MRI system 102 to receive the RF energy emitted by the precessing of the atoms within surrounding or nearby tissue. Although the RF coil 118 is depicted as a coil, it is contemplated that other loops configurations may be used.

According to one aspect, the RF coil 118 is operated in a receive mode to enable viewing of the interventional device within the body of a subject undergoing MRI analysis. For example, in addition to the MRI system 102 generating a magnetic resonance image in the usual way, the RF radiation received by the RF coil 118 is transmitted along the length of the interventional device 104 as a RF signal that is directed to the MRI system via external electronic components to be processed and combined in an appropriate way with MRI images of the subject. As a result, the RF coil 118 enables visualization of the interventional device 104 within the subject 108. This procedure describes operating the RF coil 118 in a receive mode.

According to another aspect, the RF coil 118 is operated in a transmit mode. In a transmit mode, the electrical signals are applied to the RF coil 118. The RF coil 118 produces RF electromagnetic radiation in response to the electrical signals. Generally, this RF radiation will be of much lower strength than one could generate with the external device of the MRI system. Consequently, many applications will only use the interventional device 104 in a receive mode. However, the general concepts of the invention include the use of the interventional in receive and/or transmit modes.

During operation of the MRI system 102, eddy currents can be induced in the RF coil 118 due to resonant conditions generated by the operation of the gradient coil. In particular, the current pulses that are applied (e.g., as part of a pulse sequence) to the gradient coils to generate time-varying magnetic fields can induce eddy currents in the RF coil 118. The induced eddy currents cause distortions of MRI images and generate heat in the RF coil 118, which can damage tissue within the subject.

The adaptive detuning circuit 106 enables externally coupling an impedance component to the interventional device 104 to dynamically vary the impedance of the interventional device 104. Varying the impedance of the interventional device 104 disrupts the generation of resonant conditions in the interventional device 104 and, thus, avoids the generation of undesired current within the interventional device 104. The impedance of the interventional device 104 will vary based on the amount (i.e., insertion length) and/or orientation of the interventional device 104 within the body of the subject 108. The lower the impendence in the interventional device 104, the higher the induced eddy currents. As described in more detail below, the adaptive detuning circuit 106 varies the impedance of the interventional device 104 based on detected current levels in the interventional device 104. As a result, the adaptive detuning circuit 106 adjusts impedance to a first level when the interventional device 104 is inserted a first length within the body of the subject 108 and adjusts impedance to a second level when the conducting wire is a second length within the body of the subject 108.

FIG. 2A depicts an exemplary interventional device 104 in the form of a guidewire 202A. In this example, the guidewire 202A includes a flexible lumen 204 that includes a loopless forward RF coil 206, and a microcoaxial cable 208 having an inner conductor 210. The inner conductor 210 extends in the direction of the distal end 212 of the guidewire 202A to form the RF coil 206. Platinum-iridium, insulated copper and insulated gold are all suitable materials for the inner conductor 210 and RF coil 206. A shield 214 of the microcoaxial cable 208 terminates approximately 1 cm from the distal end 212 of the guidewire 202A. The shield 214 is for example flexible nitinol hypotube.

FIG. 2B depicts another exemplary interventional device 104 in the form of a guidewire 202B. In this example, the guidewire 202B also includes the flexible lumen 204, the loopless forward RF coil 206, a microcoaxial cable 208 having an inner conductor 210, and a shield 214. The guidewire 202B also includes a dipole rod or wire 216. The dipole rod 216 extends along the length of the guidewire 202B. The dipole wire 216 and RF coil 206 operate as antennas and are matched and tuned to the Lamour frequency of the MRI system 102. The dipole wire 216 and RF coil 206 receive RF radiation generated by surrounding tissue in response to the external RF radiation applied by the MRI system 102.

FIG. 3A depicts an exemplary circuit diagram of the adaptive detuning circuit 106. According to one aspect, the adaptive detuning circuitry 106 comprises a balun circuit 302, a matching circuit 304, a detuning circuit 306, and a control circuit 308.

The balun circuit 302 balances impedances between the interventional device 104 and the MRI system 102. According to one aspect, the balun circuit 302 includes a capacitor 310, a varactor 312, and inductors 316 and 318. The balun circuit 302 is coupled to the interventional device 104 and converts the low impedance of the interventional device 104 to the high impedance of the MRI system. For example, the microcoaxical cable 208 is connected at the proximal end of the interventional device 104 to the balun circuit 302 via a connector 320, such as a micro mate connector.

The matching circuit 304 is configured to dynamically vary the impedance of the inner conductor 210 to disrupt resonant conditions of the conducting wire and avoid current and/or voltage built-up on the wire. The matching circuit 304 includes reactive elements including, for example, at least one inductor 322 to tune the conductive components (e.g., RF coil and inner conductor 210) of the interventional device 104 to resonate at the MRI frequency. In addition, matching circuit 304 includes capacitors 324, 326 and a varactor capacitor 328 that can be adjusted so that the impedance at the interventional device MRI output connections 330, 332 is matched approximately to the characteristic impedance of the microcoaxial cable 208 used to connect the interventional device 104 to the adaptive detuning circuitry 106.

The detuning circuit 306 decouples the RF coil 118 from the MRI system 102 by using a switching diode 334 to selectively connect and disconnect the segmented RF coil 118 in response to a DC control signal. For example, during MRI excitation by the body coil 109, a DC bias voltage is provided to the detuning circuit 306 from the control circuit 308 which causes the diode 334 to conduct. During conduction of the diode 334, the matching circuit 304 is shorted, which results in the detuning of the interventional device 104 and high impedance in the interventional device 104.

As described above, electrical eddy currents induced in the interventional device 104 during operation of the MRI system 102 can cause dangerous local heating in tissue. The amount of induced current and/or voltage (and the impedance thereof) on a conducting wire can be influenced by the length of the conducting wire and/or the orientation of the wire within the body of a subject. For example, when a cable has a length of a half wavelength or longer, the induced currents and/or voltages on the cable can increase significantly. On the other hand, when the cable length is smaller than quarter wavelength, the induced currents and/or voltages on the cable are generally small. Accordingly, the amount of current induced into the interventional device depends in part on the amount (i.e., length) of the interventional device that has been inserted into the body of the subject.

Figure 4:
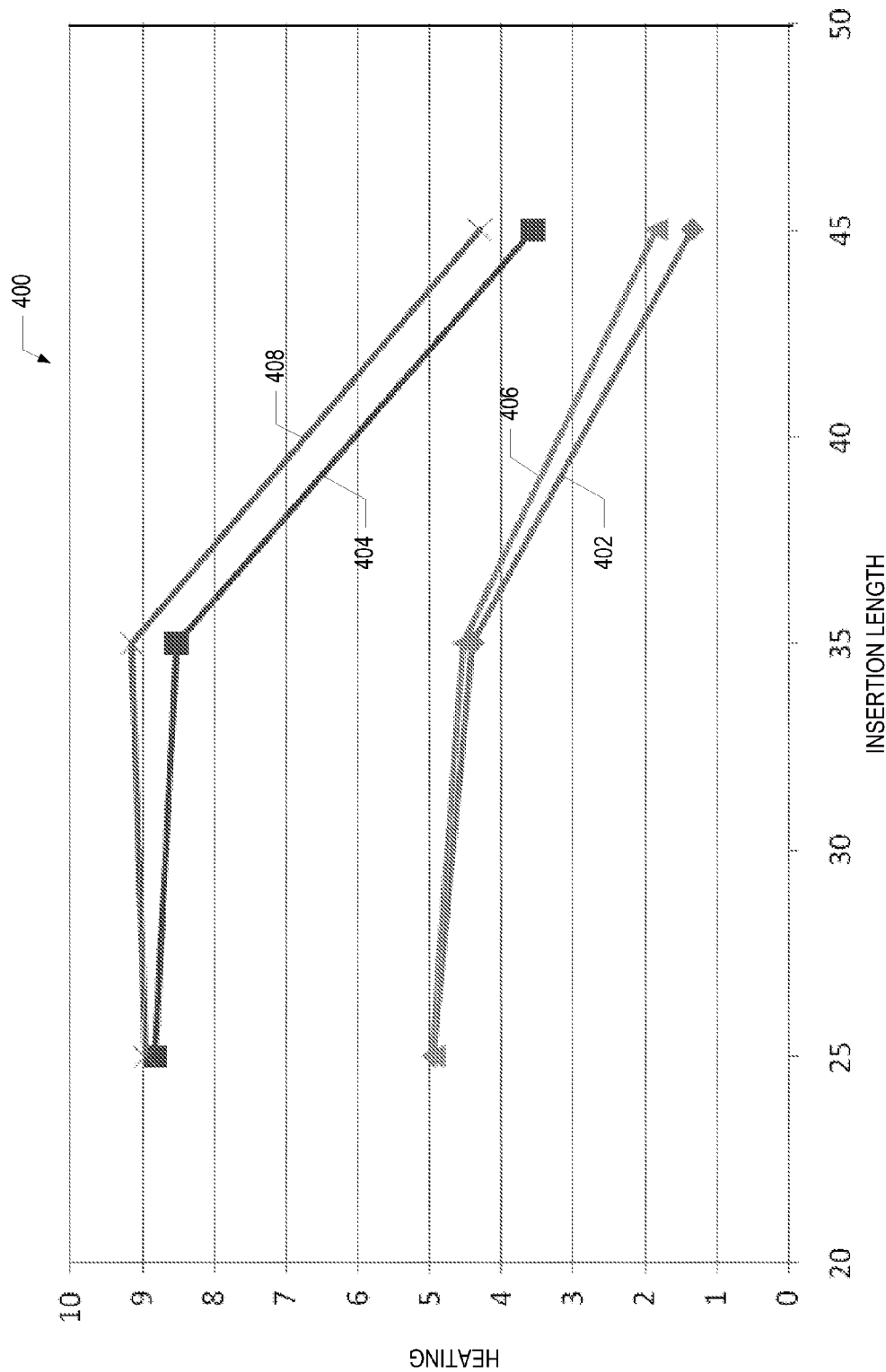
FIGS. 4 and 5 are graphs illustrating temperature profiles.

FIG. 4 is a graph 400 that depicts observed temperature profiles for an interventional device inserted into a simulated subject. In particular, graph 400 depicts temperature profiles 402, 404, 406, and 408 that correspond to heating that occurs to an interventional device inserted into a simulated subject at a 5 inch horizontal offset, 6 centimeter depth at different exemplary detuning and balun capacitance values as the insertion length varies. In the this exemplary graph 400, the illustrated profiles all correspond to interventional device inserted into a simulated subject at a 5 inch horizontal offset and 6 centimeter depth. Temperature profile 402 corresponds to heating at the tip of the interventional device 104 when the detuning capacitance has value of 15 picofarads (pF) and the balun circuit capacitance has value of 27 pF. Temperature profile 404 corresponds to heating that occurs at the tip of the interventional device when the detuning capacitance has value of 47 picofarads (pF) and the balun circuit capacitance has value of 27 pF. Temperature profile 406 corresponds to heating that occurs at the tip of the interventional device when the detuning capacitance has value of 15 picofarads (pF) and the balun circuit capacitance has value of 33 pF. Temperature profile 408 corresponds to heating that occurs at the tip of the interventional device when the detuning capacitance has value of 47 picofarads (pF) and the balun circuit capacitance has value of 33 pF. As can be observed from the graph 400, the temperature at the tip of the interventional device is lower across the insertion length when the detuning capacitance has value of 15 pF.

Figure 5:
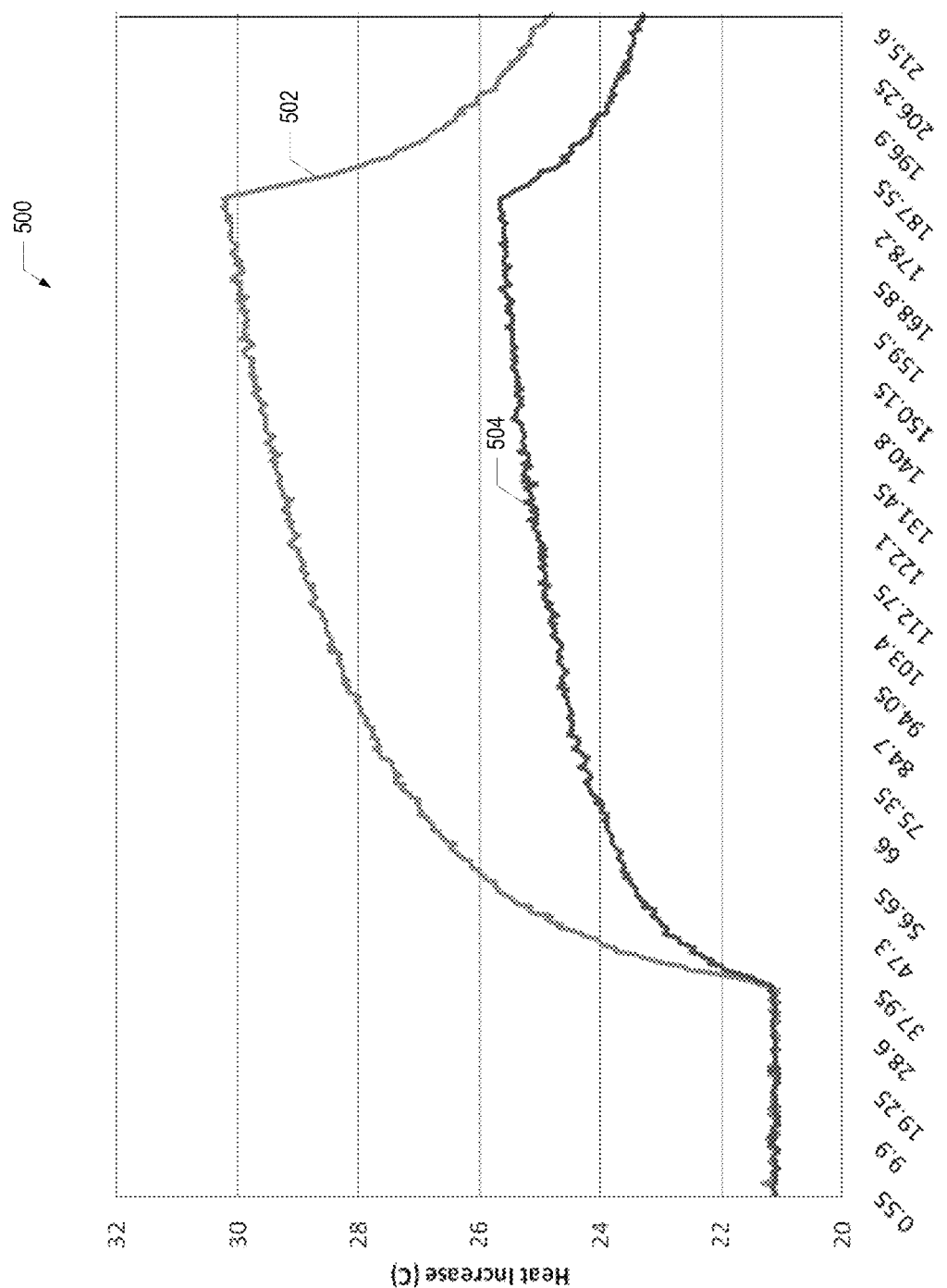

FIG. 5 is a graph 500 that depicts observed temperature profiles for an interventional device inserted into a simulated subject. In particular, graph 500 depicts temperature profiles 502, 504 that correspond to heating that occurs over time at the tip of the exemplary interventional device when the interventional device is inserted into a simulated subject at a horizontal offset of 5 inches, a depth of 6 centimeters (cm), and at an insertion length of 35 cm for different detuning capacitance values. Temperature profile 502 corresponds to heating that occurs at the tip of the interventional device when the detuning capacitance has value of 47 pF. Temperature profile 504 corresponds to heating that occurs at the tip of the interventional device when the detuning capacitance has value of 15 pF. Again, as can be observed from the graph 500, the temperature at the tip of the interventional device is lower overtime when the detuning capacitance has value of 15 pF. In addition, as can be observed from the graph 500, the change or increase in temperature at the tip of the interventional device that occurs over time is less when the detuning capacitance has value of 15 pF.

Referring back to FIG. 3, according to another aspect, the control circuit 308 detects the magnitude of the eddy current signals generated in the interventional device 104 during RF transmission phase. The control circuit 308 includes a varactor 336 that is adjusted based on the detected magnitude of current signal to adjust the detuning capacitance value of the adaptive detuning/matching circuit 106. By adjusting the capacitance of the adaptive detuning system, the impedance of the interventional device is adjusted.

According to one aspect, the control circuit 308 includes a processor, a microcontroller, or other processing device, that changes the detuning capacitance value by executing a basic averaging algorithm that sweeps the predetermined capacitor range during each repetition time of MRI sequence.

According to one aspect, the control circuit 308 adjusts the capacitance value in predetermined increments, which causes the magnitude of the current signals in the RF coil 118 to be adjusted. For example, if the magnitude of current signals in the RF coil 118 and/or the inner conductor 210 detected by the control circuit 308 during RF transmission phase is above a threshold current level, the control circuit 308 decreases the capacitance value by a predetermined amount. The control circuit 308 then detects the adjusted magnitude of the current signals in the RF coil and or dipole coil during RF transmission phase and compares the adjusted magnitude of the current to a threshold current range. If the adjusted magnitude of the current signal is still above the threshold current level, the control circuit 308 again decreases the capacitance value by predetermined amount. This iterative process continues until the magnitude of current signals in the RF coil 118 detected by the control circuit 308 during RF transmission phase is below the threshold current level.

According to another aspect, the control circuit 308 adjusts the detuning capacitance to at least eight different capacitance values during each repetition time (TR) of the MRI sequence across a range of predetermined capacitance values. For each different capacitance value, the control circuit 308 detects and records the magnitude of the corresponding current signal. The control circuit 308 adjusts the detuning capacitance to the first of the eight capacitance values that corresponds to a current signal that has a magnitude below the threshold current level. As a result, the control circuit 308 quickly changes the detuning capacitor value within each repetition time (TR) and, thus, can prevent heating of the interventional device 104 from exceeding safe operational limits.

Those skilled in the art will appreciate that variations from the specific embodiments disclosed above are contemplated by the invention. The invention should not be restricted to the above embodiments, but should be measured by the following claims.

What is claimed is:

1. An active adaptive detuning system for use during a magnetic resonance imaging procedure, the system comprising:
   a magnetic resonance imaging system to:
      apply a radio frequency radiation signal across a selected portion of a subject; and
      discontinue application of the radio frequency radiation signal across the selected portion of the subject;
   an interventional device for insertion into the subject and proximate to the selected portion of the subject, the interventional device comprising:
      a radio frequency antenna at a distal end of the interventional device to receive an induced current based on another radio frequency signal emitted from tissue surrounding the radio frequency antenna when the interventional device is inserted in the subject; and an inner conductor along a length of the interventional device and connected to the radio frequency antenna to conduct the induced current;

an adaptive detuning circuit connected to the inner conductor to:

iteratively adjust an impedance value of the interventional device through each of a plurality of impedance values;

determine a corresponding magnitude of the induced current in the inner conductor for each of the plurality of impedance values; and set the impedance value of the interventional device to a first one of the plurality of impedance values where the corresponding magnitude of the induced current is below a threshold current level to limit heating of the interventional device when inserted within the subject;

the adaptive detuning circuit comprising:

a balun circuit to balance impedances between the interventional device and the magnetic resonance imaging system;

a matching circuit to dynamically vary the impedance value of the inner conductor to disrupt resonant conditions;

a detuning circuit to connect and disconnect the radio frequency antenna from the magnetic resonance imaging system in response to a DC control signal; and a control circuit to:

generate the DC control signal when the magnetic resonance imaging system applies the radio frequency radiation signal;

detect the magnitude of the induced current in the inner conductor;

retrieve the threshold current level from a memory;

iteratively adjust the impedance value by adjusting an adaptive detuning capacitance of the adaptive detuning circuit through a series of detuning capacitance values based on the detected magnitude of the induced current;

determine the corresponding magnitude of the induced current in the inner conductor for each of the detuning capacitance values;

compare the corresponding magnitude of each induced current to the threshold current value; and set the detuning capacitance value to a first one of the detuning capacitance values where the corresponding magnitude of the induced current is below the threshold current level.

2. The active adaptive detuning system of claim 1 wherein the control circuit adjusts a varactor to adjust the detuning capacitance value.

3. The active adaptive detuning system of claim 1 wherein the series of detuning capacitance values includes at least eight different detuning capacitance values.

4. The active adaptive detuning system of claim 1 wherein the inner conductor is a microcoaxial cable.

5. An adaptive detuning circuit for use in a magnetic resonance system during insertion of an interventional device into a subject during a magnetic resonance imaging procedure, wherein the magnetic resonance imaging system applies and discontinues application of a radio frequency radiation signal across a selected portion of a subject, and wherein the interventional device comprises a radio frequency antenna to receive an induced current based on another radio frequency signal emitted from tissue proximate to the radio frequency antenna and an inner conductor connected to the radio frequency antenna to conduct the induced current conductor, the adaptive detuning circuit to:

iteratively adjust an impedance value of the interventional device through each of a plurality of impedance values;

determine a corresponding magnitude of the induced current in the inner conductor for each of the plurality of impedance values; and set the impedance value of the interventional device to a first one of the plurality of impedance values where the corresponding magnitude of the induced current is below a threshold current level to limit heating of the interventional device when inserted within the subject;

wherein the adaptive detuning circuit comprises:

a connector to connect to the inner conductor;

a balun circuit to balance impedances between the interventional device and the magnetic resonance imaging system;

a matching circuit to dynamically vary the impedance value of the inner conductor to disrupt resonant conditions; and a detuning circuit to disconnect the radio frequency antenna from the magnetic resonance imaging system in response to a DC control signal; and a control circuit to:

generate the DC control signal when the magnetic resonance imaging system applies the radio frequency radiation signal;

detect the magnitude of the induced current in the inner conductor;

retrieve a threshold current level from a memory;

iteratively adjust the impedance value by adjusting an adaptive detuning capacitance value of the adaptive detuning circuit through a series of detuning capacitance values based on the detected magnitude of the induced current;

determine a corresponding magnitude of the induced current in the inner conductor for each of the detuning capacitance values;

compare the corresponding magnitude of each induced current to the threshold current value; and set the detuning capacitance value of the interventional device to a first one of the detuning capacitance values where the corresponding magnitude of the induced current is below the threshold current level.

6. The adaptive detuning circuit of claim 5 wherein the control circuit adjusts a varactor to adjust the detuning capacitance value.

7. A method for adjusting an impedance value associated with an interventional device during insertion of the interventional device into a subject during a magnetic resonance imaging procedure, the method comprising:

inserting an interventional device having an inner conductor and a radio frequency antenna into the subject;

applying a radio frequency radiation signal across a selected portion of a subject via a magnetic resonance imaging system;

discontinuing application of the radio frequency radiation signal across the selected portion of the subject;

receiving an induced current in the conductor via the radio frequency antenna based on another radio frequency signal emitted from tissue surrounding the radio frequency antenna when application of the radio frequency radiation signal is discontinued;

balancing impedances between the interventional device and magnetic resonance imaging system;

disconnecting the radio frequency antenna from the magnetic resonance imaging system in response to a DC control signal;

generating the DC control signal when the radio frequency radiation signal is being applied;

detecting the magnitude of the induced current in the inner conductor;

retrieving a threshold current level from a memory, wherein the threshold current level limits heating of the interventional device when inserted within the subject;

iteratively adjusting an impedance value of the interventional device by adjusting an adaptive detuning capacitance value through a series of detuning capacitance values based on the detected magnitude of the induced current;

determining a corresponding magnitude of the induced current in the inner conductor for each of the detuning capacitance values;

comparing the corresponding magnitude of each induced current to the threshold current value; and setting the detuning capacitance value of the interventional device to a first one of the detuning capacitance values where the corresponding magnitude of the induced current is below the threshold current level.

8. The method of claim 7 further comprising adjusting a varactor to adjust the detuning capacitance value.

9. The method of claim 7 wherein the series of detuning capacitance values includes at least eight different detuning capacitance values.

* * * * *